United States Patent [19]

Clark et al.

[11] Patent Number: 5,547,681
[45] Date of Patent: Aug. 20, 1996

[54] DERMAL PATCH

[75] Inventors: Elke M. A. Clark, Ringoes; Lawrence Marlin, Bridgewater; You-Ling Fan, East Brunswick; Harshad M. Shah, Edison, all of N.J.

[73] Assignee: Union Carbide Chemicals & Plastics Technology Corporation, Danbury, Conn.

[21] Appl. No.: 274,834

[22] Filed: Jul. 14, 1994

[51] Int. Cl.$^6$ .................. A61F 13/00; A61F 13/02; A61K 9/14
[52] U.S. Cl. ................ 424/449; 424/486; 604/307
[58] Field of Search .................... 604/304, 307; 424/449, 447, 486; 525/61

[56] References Cited

U.S. PATENT DOCUMENTS

| | | | |
|---|---|---|---|
| 2,720,468 | 10/1955 | Shacklett . | |
| 3,318,856 | 5/1967 | Deyrup . | |
| 3,839,307 | 10/1974 | Schmifg | 525/61 |
| 4,492,685 | 1/1985 | Keith | 424/28 |
| 4,524,064 | 6/1985 | Nambu | 424/81 |
| 4,552,138 | 11/1985 | Hofeditz et al. | 128/156 |
| 4,908,213 | 3/1990 | Govil | 424/447 |
| 4,943,435 | 7/1990 | Baker | 424/448 |
| 5,008,110 | 4/1991 | Benecke | 424/448 |
| 5,016,652 | 5/1991 | Rose | 131/270 |
| 5,128,124 | 7/1992 | Fankhauser et al. | 424/449 |
| 5,176,915 | 1/1993 | Hoffmann | 424/445 |
| 5,246,706 | 9/1993 | Chiang | 424/449 |
| 5,260,066 | 11/1993 | Wood et al. | 424/447 |

FOREIGN PATENT DOCUMENTS 0107376  9/1983  European Pat. Off. .

*Primary Examiner*—David H. Willse
*Assistant Examiner*—David J. Cho
*Attorney, Agent, or Firm*—W. K. Volles

[57] ABSTRACT

Dermal patches containing a flexible, crosslinked, polymeric gel comprising polyvinyl alcohol and a crosslinking agent comprising a multivalent element, e.g., titanium complexed with hydroxyalkyl amines, are disclosed. The dermal patches can be used to deliver pharmaceutically active agents to the dermal surface of a mammal, or alternatively can be used without the pharmaceutically active agents. The dermal patches have properties, such as, for example, a high degree of water absorbency, oxygen permeability and physiological compatibility which render them suitable for treatment of open skin, e.g., lacerations, burns or blisters, as well as unbroken, intact skin.

9 Claims, 1 Drawing Sheet

DERMAL PATCH

FIELD OF THE INVENTION

The present invention generally relates to dermal patches which are suitable for application to the dermal surface of a mammal. More specifically, the present invention relates to dermal patches which are based on a flexible, cross linked polymeric gel comprising polyvinyl alcohol and a cross linking agent comprising a multivalent transition element.

BACKGROUND OF THE INVENTION

The delivery of pharmaceutically active agents by way of dermal patches has become increasingly popular in recent years. Dermal patches are often employed when it is desired to obtain a controlled release of a pharmaceutically active ingredient over time, e.g. from several hours to several days or weeks. In addition, dermal patches are often utilized to deliver a pharmaceutically active agent to a specific area of the skin. Notable recent uses of dermal patches have been in, for example, the transdermal delivery of nicotine which has been helpful for some humans to curb the urge to smoke.

Typically, dermal patches used for the delivery of a pharmaceutically active agent to the skin comprise an internal reservoir or a polymer matrix as a carrier for the pharmaceutically active agent which is supported by protective skins, e.g., polyethylene, for structural integrity. Although such dermal patches typically function well when in contact with intact, unbroken skin, they often offer little or no significant benefit when used in contact with open skin, e.g., lacerated, burned or blistered skin.

Polymeric gels based on hydrated polymers have been proposed for use in treating lacerations, burns and blisters on the skin. Such polymeric gels are typically cross linked to provide structural integrity. However, typical cross linking techniques have disadvantages associated therewith. For example, gamma irradiation has been used to gel aqueous polymer solutions which can provide a gel having adequate structural integrity. Such irradiated gels may be physiologically compatible. However, the irradiation can delitirously affect any pharmaceutically active agents present in the gel. Therefore, they are unsuitable for delivery of pharmaceutically active agents. Gels cross linked with aldehydes, such as, formaldehyde, or glutaraldehyde have also been proposed. However, gels cross linked with such aldehydes may not be physiologically compatible and therefore may not be suitable for use in contact with skin. In addition, boric acid, and sodium tetraborate have been proposed to gel polymeric solutions. This reaction, however, necessitates a pH of 9 or greater which is not desirable for use in contact with skin.

Accordingly, dermal patches which are physiologically compatible, suitable for use in contact with open skin and able to carry and deliver a pharmaceutically active agent are desired.

SUMMARY OF THE INVENTION

By the present invention, dermal patches are provided which have a high degree of flexibility and structural integrity, are physiologically compatible, have good oxygen permeability and a high water content, and can carry and deliver pharmaceutically active agents. By virtue of the present invention, it is now possible to deliver a pharmaceutically active agent to the dermal surface of a mammal, whether or not the skin is intact or open. In addition, the dermal patches of the present invention can exhibit wound healing properties. Thus, the dermal patches can be used, if desired, without a pharmaceutically active agent.

DETAILED DESCRIPTION OF THE INVENTION

Figure 1:
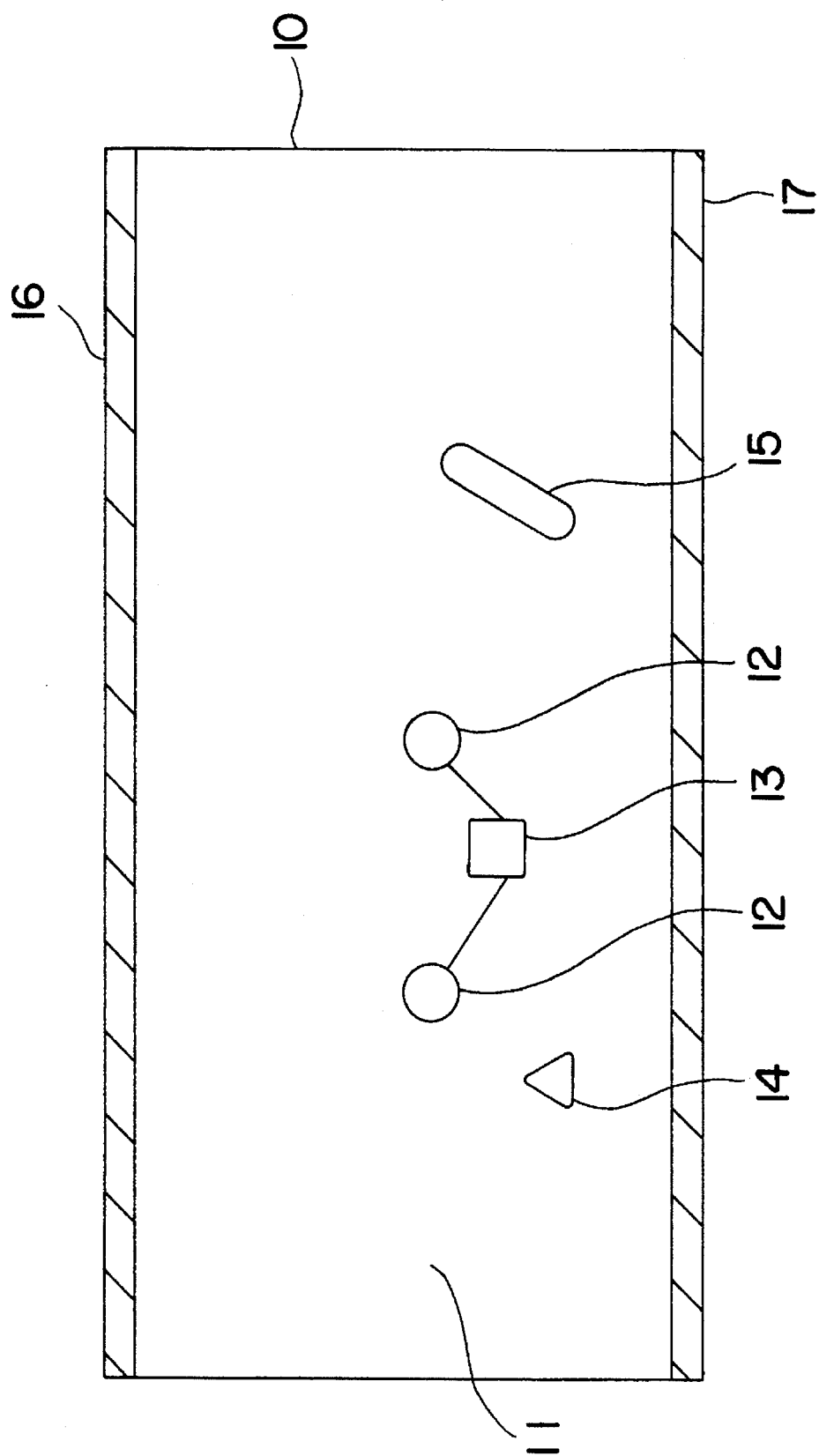
FIG. 1 is a cross-sectional schematic of a dermal patch in accordance with the present invention.

The dermal patches of the present invention are suitable for use on the dermal surfaces of mammals. As used herein, the term "dermal surface" means: (1) intact, unbroken skin; (2) skin which is open, e.g., lacerated, burned, blistered and the like; and (3) mucosal tissue. As used herein, the term "mammals" means any class of higher vertebrate that nourish their young with milk secreted by mammary glands, e.g., humans, rabbits and monkeys.

The invention is hereafter described with reference to FIG. 1 which is presented for illustrative purposes and is not intended to limit the scope of the claims which follow.

FIG. 1 illustrates a cross sectional schematic of a dermal patch 10 in accordance with present invention.

The dermal patch comprises an internal matrix (11) which comprises a flexible cross linked polymeric gel. The gel comprises: from about 2 to 14 weight percent, preferably from about 5 to 9 percent polyvinyl alcohol (12); from about 1.6 to 11 weight percent, preferably from about 1.6 to 5 weight percent, and more preferably from about 1.6 to 3.2 weight percent of a cross linking agent comprising a multivalent transition element (13); and from about 25 to 95 weight percent, preferably from about 75 to 93 weight percent water (14); said percentages based on the total weight of the polymeric gel. The schematic representation of FIG. 1 shows that two polyvinyl alcohol molecules (12) are bonded by cross linking agent (13).

As used herein, the term "polyvinyl alcohol" refers to the product obtained by replacing all or a portion of the acyl groups in a polyvinyl ester with hydroxyl groups. Well known methods of preparing polyvinyl alcohol include hydrolysis, alcoholsis or saponification of a polyvinyl ester. Suitable polyvinyl esters include polyvinyl formate, polyvinyl acetate, polyvinyl propionate, polyvinyl butyrate and the like. A preferred polyvinyl ester is polyvinyl acetate.

The polyvinyl alcohols suitable for use in accordance with the present invention may be homopolymers or copolymers. Preferably, in the prehydrolyzed copolymer, at least 50 mole percent, more preferably at least 75 mole percent, and most preferably, at least 85 mole percent of the monomeric units are polyvinyl esters. Any olefinically unsaturated monomers which will copolymerize with polyvinyl esters may be used for preparing the polyvinyl alcohol copolymers used in the dermal patches of the present invention. The details concerning the preparation of such copolymers including the selection of suitable comonomers, are known to those skilled in the art.

The polyvinyl alcohols suitable for use in accordance with the present invention typically have a molecular weight of from about 31,000 to 186,000 grams per gram mole, preferably from about 85,000 to 186,000 grams per gram mole, and more preferably from about 90,000 to 130,000 grams per gram mole. As used herein, the term "molecular weight" means weight average molecular weight. Methods for determining weight average molecular weight of polyvinyl alcohols are known to those skilled in the art. One method for determining molecular weight is low angle laser light scattering. The viscosity of the polyvinyl alcohols typically ranges from about 27 to 75 centipoise and preferably from about 40 to 60 centipoise. Unless otherwise indicated, as used herein the term "viscosity" refers to the viscosity of a 4.0 weight percent aqueous solution of the polymer measured at 20° C. with a Brookfield viscometer. Such viscosity measuring techniques are known to those skilled in the art.

Typically, the polyvinyl alcohols of the present invention have a degree of hydrolysis of at least about 88%, preferably from about 88 to 99 percent and a more preferably from about 96 to 99 percent. As used herein, the term "degree of hydrolysis" means the portion of hydrolyzable groups, e.g., acyl groups in the original polymer which have been replaced by hydroxyl groups. In the case of polyvinyl alcohol homopolymers, the degree of hydrolysis can be calculated by dividing the average number of hydroxyl groups in the polyvinyl alcohol homopolymer by the total average number of acyl groups in the original polyvinyl ester. In the case of polyvinyl alcohol copolymers, the degree of hydrolysis can be calculated by dividing the average number of hydroxyl groups in the polyvinyl alcohol copolymer by the total number of hydrolyzable groups in the original copolymer. Methods for determining the degree of hydrolysis are known to those skilled in the art.

Multivalent transition elements suitable for use as crosslinking agent (13) are identified for example, in the periodic table of the elements published in the Handbook of Chemistry and Physics 56 Edition, CRC Press, Cleveland, Ohio 1975. Preferred multivalent transition elements include titanium, chromiun and vanadium. It is also preferred that the multivalent transition elements are capable of crosslinking the polyvinyl alcohol at a pH of from about 4 to 8, preferably from about 5 to 7.5 in an aqueous medium at a temperature of from about 10° to 30° C. at a pressure of about 1 atm within a reaction time of less than about 30 minutes, preferably less than about 10 minutes.

Especially preferred crosslinking agents are those which comprise a titanium complex selected from the group consisting of:

(i) titanium complexes with tri(hydroxyl alkyl) amines containing from 2 to 6 carbon atoms; and (ii) titanium complexes with diketones containing from 5 to 20 carbon atoms.

Typical examples of such amines include triethanolamine, tripropylamine, triisopropylamine, tributylamine, trihexanolamine, mixed hydroxyalkylamines and mixtures thereof. Typical diketones include 2,4-pentanedione, 2,4-hexanedione, 2,4-heptanedione, 5-methyl-2,4-hexanedione, 2,4-octanedione, 5,5-dimethyl-2,4-hexanedione, 3-ethyl-2,4-pentanedione, 2,4-decanedione, 2,2-dimethyl-3,5-nonanedione, 3-methyl-2,4-pentanedione, 2,4-tridecanedione, 1-cyclohexyl-1,3-butanedione, 5,5-dimethyl- 1,3-cyclohexanedione, 1,3-cyclohexanedione, 1-phenyl-1,3-butanedione, 1(4-biphenyl)-1,3-butanedione, 1-phenyl-1,3-pentanedione, 3-benzyl-2,4-pentanedione, 1-phenyl-2-butyl-1,3-butanedione, and dibenzoylmethane. A preferred diketone is 2,4-pentanedione.

Preferably, the crosslinking agent is incorporated in an amount sufficient to provide the desired structural integrity. In general, low concentrations of the crosslinking agent tend to decrease the structural integrity whereas high concentrations of the crosslinking agents enhance the structural integrity. However, high concentrations of the crosslinking agent also tend to decrease flexibility and provide a dermal patch which has a rubbery consistency. Thus, in accordance with the present invention, the concentration of crosslinking agent is maintained within a range which provides the dermal patch with a high degree of structural integrity while retaining a high degree of flexibility. Preferably, the dermal patches of the present invention have a sufficient degree of flexibility to conform to the topography of the dermal surface upon which it is placed, e.g., over the joint of a knuckle.

The internal matrix may also optionally include one or more pharmaceutically active agents (15). As used herein, the term "pharmaceutically active agent" means any element or compound which has an effect on the physiology of a mammal. The pharmaceutically agent may, for example, have a therapeutic or diagnostic effect. Typical pharmaceutically active agents include, for example, analgesic agents, anti-inflammatory agents, anti-itch agents, antibiotics, medicinal agents, anesthetics and the like. Details concerning the selection and amounts of such pharmaceutically active agents are known to those skilled in the art. However, such pharmaceutically active agents are typically present in an amount of from about 0.01 to 50 weight percent, although higher and lower concentrations are within the scope of the present invention.

If desired, the inner matrix may also comprise other ingredients, such as, for example, preservatives, colorants and fragrances (not shown in FIG. 1), the details of which are known to those skilled in art. In addition, if desired the inner matrix may also contain reinforcing materials, such as, for example, nylon gauze, rayon mesh, as well as other reinforcing materials known to those skilled in the art (not shown in FIG. 1).

The dermal patches of the present invention also comprise an outer surface (16) and an inner surface (17). The outer and inner surfaces may be comprised of the same ingredients which comprise the inner matrix or alternatively may be comprised of different ingredients. Thus, if desired, an additional material, e.g., a protective skin, such as for example, polyethylene, polypropylene, polyvinyl chloride, cellophane and the like, may be used as to comprise the outer surface (16) or inner surface (17). However, when multivalent titanium complexes are used as a crosslinking agent in accordance with a preferred aspect of the present invention, the inner matrix 11 typically has sufficient structural integrity to obviate the need for protective skins surrounding the inner matrix. Thus, it is preferred that the inner surface, and more preferably both the inner surface and the outer surface, comprise the same ingredients as those which comprise the inner matrix. Since the dermal patches of the present invention are often subjected to drying and irradiation for sterilization purposes (described in more detail below), the degree of hydrolysis, extent of oxidation and crosslinking may be different on the outer and inner surfaces than in the inner matrix. By utilizing the same ingredients in the outer and inner surfaces, the dermal patches of the present invention can quite advantageously retain the beneficial attributes of polymeric gels. Such benefits include for example, a high degree of oxygen permeability, a high water content, transparency, physiological compatibility and absorbtivity. When such attributes are desired, it is generally not preferred to utilize a protective skin such as described above to comprise inner surface (17) since such protective skins often do not have the beneficial wound healing attributes of the inner matrix described above.

Quite advantageously in accordance with the present invention, the inner surface (17) is removably adherent to the dermal surface. As used herein, the term "removably adherent" means that the dermal patch can be removed from the dermal surface of a mammal while retaining its structural integrity and thereafter be replaced onto the dermal surface. This feature facilitates the removal of the dermal patch for inspection of the skin, laceration, blister, etc., beneath the dermal patch. In addition, the dermal patches of the present invention are preferably substantially transparent which permits inspection of the covered dermal surface without removing the dermal patch.

Moreover, the dermal patches of the present invention are highly absorbent. In fact, the dermal patches of the present invention are typically able to adsorb from about 2 to 3 times their weight or more of water in addition to the water originally present in the dermal patch. This is a great advantage with respect to the treatment of burns and lacerations, so that exuded matter formed during the healing process may be absorbed and diffused away from the treated area.

The processes of the present invention for preparing the dermal patches preferably comprise: (1) preparing a first solution of the polyvinyl alcohol homopolymer or copolymer in water; (2) preparing a second solution of the crosslinking agent in a suitable solvent, e.g., water or water/alcohol mixture; (3) combining the first solution and the second solution at a molar ratio of from about 63:1 to 8.5:1 and preferably from about 50:1 to 30:1, based upon the average moles of hydroxyl groups on the polymer to moles of multivalent transition element; (4) transferring the combined solutions to a suitable support, such as, for example, a polyethylene sheet, silicone release paper, or urethane dermal patch, to form a sheet of crosslinked or partially crosslinked polymer gel at a thickness of from about 40 to 250 thousanths of an inch ("mil") and preferably from about 50 to 125 mil; and (5) curing the mixture to from a gel-like structure at room temperature, or e.g., by heating in a convection oven or with an infrared heating lamp to acccelerate the crosslinking.

Preferably, the first solution of polyvinyl alcohol is made by combining the polyvinyl alcohol with water at a concentration of from about 5 to 10 weight percent polyvinyl alcohol and heating the mixture to about 85–95° C. while stirring. The dissolution process for the polyvinyl alcohol typically takes from about 30 to 60 minutes in the temperature range noted above. Of course, higher or lower temperatures can be employed depending upon factors known to those skilled in the art, such as, for example, the degree of hydolysis of the polymer and desired dissolution time. After dissolution, the polyvinyl alcohol solution is then preferably cooled to about room temperature.

The second solution is preferably prepared by combining the crosslinking agent with the desired solvent, e.g., distilled water, at a concentration of from about 16 to 40 weight percent of the crosslinking agent. It is typically not necessary to heat the combination of the crosslinking agent and solvent in order to effect the dissolution.

A preferred method of curing the polymer gel is to heat the gel at a temperature of from about 80° to 125° C. for a time from about 5 to 10 minutes in an oven or by means of any other thermal heating device such as, an infrared heating lamp.

In preparing the dermal patches of the present invention, it is often desirable to incorporate a buffer prior to the crosslinking of the polymer solution in order to adjust the pH of the final dermal patch to from about 4 to 8 and preferably from about 5 to 7.5. Dermal patches prepared from solutions in the above pH ranges are desirable since they are generally compatible with the pH of dermal surface.

Other ingredients, such as, for example, pharmaceutically active agents, reinforcements, preservatives, and other additives are preferably incorporated into the polymer mix prior to crosslinking.

Further details concerning the procedures and apparatus for making the dermal patches of the present invention, including the selection and amounts of other buffers and other ingredients are known to those skilled in the art.

After crosslinking, the sheet of crosslinked polymeric gel is then preferably cut into pieces having the desired geometry, e.g., circular, square, rectangular, triangular, etc., and size. Typically, the size of the patches will range from about 1 square millimeter to about 100 square centimeters or larger for small mammals like humans or monkeys. For larger mammals, such as, for example, elephants, the dermal patches may have an area of up to 1 square meter or larger.

Typically, the dermal patches are packaged in aluminum pouches. Additionally, if it is desired to utilize protective skins, either on the outer surface or inner surface or both, such skins are typically applied prior to packaging and either prior to or subsequent to cutting the crosslinked polymeric gel.

It is often desirable to sterilize the dermal patches, particularly when the patches will be in contact with open skin. Typical methods for sterilization include irradiation and treatment with ethylene oxide, the details of which are known those skilled in the art. Irradiation can be performed either prior to or after packaging.

Further details concerning packaging, sterilization, and the application of protective skins are known to those skilled in the art.

The dermal patches of the present invention can be used for a variety of purposes, such as for example, to deliver a pharmaceutically active agent to the dermal surface. Moreover, as an alternative to the delivery of a pharmaceutically active agent, or in combination with such delivery, the dermal patches of the present invention can be used to promote the healing of wounds, such as for example, lacerations, burns and blisters. In some instances, such as for example, the treatment of burns, it is often desirable to saturate the dermal patches of the present invention with a physiological saline solution, i.e., 0.9 weight percent salt in water. In general, the dermal patches of the present invention can be simply applied to the dermal surface of a mammal in the desired treatment area. The dermal patches can be worn for any desired length of time consistent with acceptable medical or veterinary practices, e.g., about 1 hour to 72 hours or more. Moreover, the dermal patches can be periodically removed in order to inspect the areas of the dermal surface or wound beneath the patch.

The following examples are provided for illustrative purposes and are not to intended to limit the scope of the claims which follow. The term "parts" is made with reference to weight parts.

The following materials were used in the examples.

| DEFINITIONS OF MATERIALS | |
|---|---|
| AIRVOL ®350 - | Polyvinyl Alcohol having a degree of hydrolysis of 98–98.8% and an average molecular weight of 124,000 to 186,000 g/gmole. available from Air Products & Chemicals Inc. Allentown, PA. |
| AIRVOL 425 - | Polyvinyl Alcohol having a degree of hydrolysis of 95.5–96.5 and an average molecular weight of 85,000 to 146,000 g/gmole. available from Air Products & Chemicals Inc. Allentown, PA. |
| AIRVOL 205 - | Polyvinyl Alcohol having a degree of hydrolysis of 87–89% and an average molecular weight of 31,000 to 50,000 g/gmole. available from Air Products & Chemicals Inc. Allentown, PA. |
| AIRVOL 540 - | Polyvinyl Alcohol having a degree of hydrolysis of 87 to 89% and an average molecular weight of 124,000–186,000 g/gmole. available from Air Products & Chemicals Inc. Allentown, PA. |
| TYZOR ®TE - | a titanium complex with triethanol amine available from DuPont, Wilmington, DE. |
| TYZOR ®GBA - | A titanium chelate with acetyl acetonate available from Du Pont, Wilmington, DE |
| TYZOR ®LA - | Titanium lactic acid chelate, ammonium salt available from Du Pont, Wilmington, DE |
| TYZOR ®TBT - | Tetra-n-Butyl titanate available from Du Pont, Wilmington, DE |
| GERMALL II - | Diazolidinyl Urea available from Sutton Laboratories, Chatham, NJ |

EXAMPLE 1

Preparation of Crosslinking Solutions

Catalyst Solution A

To 2 parts of TYZOR TE were added 8 parts of distilled water. The solution was mixed and not stored longer than 8 hours prior to use.

Catalyst Solution B

To 3 parts of TYZOR TE were added 7 parts of distilled water. The solution was mixed and not stored longer than 8 hours prior to use.

Catalyst Solution C

To 4 parts of TYZOR TE were added 6 parts of distilled water. The solution was mixed and not stored longer than 8 hours prior to use.

Catalyst Solution D

To 1 part of TYZOR GBA were added 5.5 parts of methanol. After the solution was mixed, 5 parts of distilled water were added and mixed into the solution. The solution was not stored longer than 30 minutes prior to use.

Catalyst Solution E

To 4 parts of TYZOR LA were added 6 parts of distilled water. The solution was mixed and not stored longer than 8 hours prior to use.

Catalyst Solution F

To 2 parts of TYZOR TBT were addied 8 parts of anhydrous n-butanol.

EXAMPLE 2

Preparation of Dermal Patch

A dispersion was prepared by adding 5 parts of AIRVOL 425 to 2.5 parts of AIRVOL 350 in 92.5 parts of distilled water. The mixture was heated to 93° C. and stirred for one hour at this temperature. The resulting solution was cooled to room temperature.

The dermal patch was prepared by adding 1 part of the polyvinyl alcohol solution into a beaker. Under vigorous stirring, 0.1 part of the crosslinking solution A was added. The mixture was stirred for 40 seconds and left to crosslink for 4 minutes. After this time the gel was still very flowable. It was drawn down into a 125 mil thick dermal patch. The dermal patch which was wet and semi- sticky at this time was placed into an oven for 10 min. at 100° C. The resulting dermal patch was dry to the touch, clear, non adhesive and had excellent flexibility. The pH of the dermal patch was about 8.5. It contained about 75% water.

EXAMPLE 3

Preparation of Dermal Patch

This example shows the use of an alternative titanium chelate as crosslinking agent. Three (3) parts of AIRVOL 350, 6 parts of AIRVOL 425 and 0.2 part of potassium sorbate as a preservative were added to 90.8 parts of distilled water. The mixture was heated to 93° C. and held at that temperature for one hour while stirring. The mixture was brought to room temperature while stirring. Five Hundred forty-one (541) parts of this solution were diluted with 108.3 parts of distilled water. The solution was stirred for 1.5 hours to effect good mixing. 10 parts of this solution was mixed by hand with 1 part of crosslinking solution D. The mixture was stirred for 40 seconds. A dermal patch 125 mil thick was drawn onto a very thin polyurethane film (approximately 1 mil). The dermal patch had a pH of 5.5. It was placed in a 100° C. oven for 10 minutes. The dermal patch was dry to the touch, had excellent flexibility was transparent and contained about 70% of water.

EXAMPLE 4

Effect of pH

The pH of the dermal patch is important to minimize any irritation. For this purpose the patch is preferably prepared with a pH that ranges from 5.5 to 7.5. Not all titanium complexes will form hydrogels at this preferred pH range. In this example, the effect of pH on the ability of titanium catalysts to cross link polyvinyl alcohol solutions at room temperature in less than 30 minutes is demonstrated.

One part of AIRVOL 350, 6 parts of AIRVOL 425 and 0.15 parts of potassium sorbate were added to 92.75 parts of distilled water. The mixture was heated to 93° C. and held at that temperature for one half hour while stirring. The mixture was brought to 60° C. and 0.1 part of GERMALL II was added. The resulting solution was cooled to room temperature. Aliquots of this polymer solution were adjusted to have pHs varying from 4.6 to 12. Ten (10) parts of each solution was mixed with one part of crosslinking solution. The mixture was stirred for a few seconds, a final pH determination of each mixture was made as well as a determination if cross linking occured in less than 30 minutes at room temperature. Table 1 summarizes the data.

TABLE 1

Effect of pH on Cross linking Ability for various Titanium Complexes with Polyvinyl Alcohol Solutions

| Solution pH | Catalyst Solution A | Gel pH | Catalyst Solution D | Gel pH | Catalyst Solution F | Gel pH | Catalyst Solution E | Gel pH |
|---|---|---|---|---|---|---|---|---|
| 4.6 | + | 7.6 | + | 5.0 | − | 5.0 | − | 4.9 |
| 7.0 | + | 8.7 | + | 6.0 | − | 6.4 | − | 6.9 |
| 8.9 | + | 9.0 | + | 6.3 | − | 6.7 | − | 7.1 |
| 10.6 | + | 9.0 | + | 6.4 | − | 7.0 | − | 7.3 |
| 12.0 | + | 11.3 | + | 8.8 | − | 9.6 | + | 8.8 |

+ Denotes cross linking
− Denotes no gel formation

EXAMPLE 5

Effect of Molecular Weight

The following examples illustrate the effect of molecular weight and concentration on the ability to form strong dermal patches.

A solution was prepared by adding 10 parts of AIRVOL 425 to 90 parts of water into a mixing tank. The mixture was heated to 93° C. and stirred at this temperature for one hour. The resulting polymer solution was cooled to room temperature.

The polyvinyl alcohol solution and crosslinking solution C were mixed at a 10:1 weight ratio for 22 seconds. The mixture was then drawn down to a 125 mil thick dermal patch onto a polyurethane support. The pH of the dermal patch was measured to be approximately 8.5. The dermal patch was dried in a static oven at 100° C. for 10 min. The dermal patch felt dry to the touch, slightly sticky and was totally transparent. It has good strength and a somewhat rubbery consistency. The flexibility of this dermal patch was less than that observed in Example 3. The dermal patch contained about 70% water.

COMPARATIVE EXAMPLE 6

Effect of Molecular Weight

A polyvinyl alcohol solution was prepared by adding 10 parts of AIRVOL 205 to 90 parts of water into a mixing tank. The mixture was heated to 88° C. and maintained at this temperature for 45 minutes. The resulting polymer solution was cooled to room temperature.

The polyvinyl alcohol solution and crosslinking solution C were mixed at a 10:1 weight ratio for 22 seconds. No instant gelling was observed. After 15 minutes some gelling was observed. The dermal patch was dear, very weak and sticky. No cohesive, self supporting dermal patch could be formed.

COMPARATIVE EXAMPLE 7

Effect of Molecular Weight

A polyvinyl alcohol solution was prepared by adding 10 parts of AIRVOL 425 to 88.75 parts of distilled water. To this mixture was added 0.15 parts of potassium sorbate and 0.1 part of diazolidinyl urea as well as 1 part of potassium hydrogen phthalate as preservatives. The mixture was heated to 93° C. and stirred at this temperature for one hour. The resulting solution was cooled to room temperature.

Two parts of the above polymer solution were diluted with 8 parts of distilled water which contained 1% of potassium hydrogen phthalate by weight to form a 2% by weight solution of AIRVOL 425.

The polymer solution was mixed with crosslinking solution A by pumping the solutions at a 10:1 weight ratio through a static mixer. The resulting mixture had a pH of 7.2. It did not form a gel. The consistency was water like and no self supporting dermal patch could be formed.

EXAMPLE 8

Effect of Molecular Weight

A polyvinyl alcohol solution was prepared by adding 10 parts of AIRVOL 425 to 88.75 parts of distilled water. To this mixture was added 0.15 parts of potassium sorbate and 0.1 part of diazolidinyl urea as well as 1 part of potassium hydrogen phthalate as preservatives. The mixture was heated to 93° C. and stirred at this temperature for one hour. The resulting solution was cooled to room temperature.

Five parts of the above polymer solution were diluted with 5 parts of distilled water which contained 1% of potassium hydrogen phthalate by weight.

The polymer solution was mixed with crosslinking solution A by pumping the solutions at a 10:1 weight ratio through a static mixer. The resulting mixture had a pH of 7.3. A gel formed as soon as the mixture exited the static mixture. A 125 mil thick dermal patch was formed and placed for 10 min. in a 100° C. oven, the clear dermal patch felt slightly sticky. It contained about 77% water and exhibited good draping capacity.

EXAMPLE 9

Draping Distance

The flexibility of the dermal patches was determined by using the following test. All dermal patches were prepared on a very thin urethane substrate. The finished dermal patch was placed at the edge of a table with 1¼" of dermal patch extending from the edge. Due to gravity and lack of stiffness the dermal patches will fold over the edge. The greater the flexibility of the dermal patch, the closer the dermal patch will follow the contour of the table edge. Therefore, by measuring the distance of the dermal patch from the table edge ("Draping Distance") (d) we were able to quantify the flexibility of the dermal patches. The smaller the distance (d)

the better the draping capacity. Preferably, the Draping Distance is less than 7 millimeters, and more preferably less than 3 millimeters.

(A) This example and the following two illustrate the change in flexibility of the dermal patches when prepared with the same polymer concentration but with varying crosslinker concentrations. It was found that the lower the crosslinker concentration, the higher the flexibility. Six parts of AIRVOL 540 were mixed with 93.6 parts of distilled water and 0.4 parts of Germall II. The solution was heated to 85° C. and held at this temperature for 30 minutes. Then cooled to room temperature.

Ten parts of this poly(vinyl) alcohol solution were mixed by hand in a beaker with I part of catalyst solution C. A 125 mil thick dermal patch was coated on a thin polyurethane dermal patch. The dermal patch was placed in a 100° C. oven for 10 minutes. The flexibility of the dermal patch was tested with the above described procedure.

(B) A poly(vinyl) alcohol solution was prepared as in Example 10 (A). To 10 parts of this solution 1 part of crosslinking solution B was added and mixed in a beaker. A 125 mil thick dermal patch was formed following the procedure in Example 9 (A). The flexibility was measured.

(C) A poly(vinyl) alcohol solution was prepared as in Example 10 (A). To 10 parts of this solution 1 part of crosslinking solution A was added and mixed in a beaker. A 125 mil thick dermal patch was formed following the procedure in Example 9 (A). The flexibility was measured and the results are shown in Table 2 below.

TABLE 2

RESULTS OF DRAPE TEST OF EXAMPLES 9 (A), (B) AND (C)

| Example # | Polymer Concentration Weight # | Catalyst Concentration Weight % of Titanium | Drape Distance (d) mm |
|---|---|---|---|
| 8 | 5.45 | 0.30 | 8 |
| 9 | 5.45 | 0.23 | 6 |
| 10 | 5.45 | 0.15 | 3 |

EXAMPLE 10

Effect of Molecular Weight (A) This example and Example 10 (B) illustrate the effect of molecular weight on flexibility while maintaining a constant polymer concentration. The examples illustrate that high molecular weight polymer will cause a stiffening of the dermal patch. A summary is provided below.

Seven and one-half parts of AIRVOL 425 were mixed with 92.3 parts of distilled water and 0.2 parts of Germall II. The mixture was heated to 92° C. and agitated at this temperature for 1 hour. The poly(vinyl) alcohol solution was cooled to room temperature.

Ten parts of this poly(vinyl) alcohol solution were mixed by hand in a beaker with 1 part of catalyst solution C. A 125 mil thick dermal patch was coated on a thin polyurethane dermal patch. The dermal patch was placed in a 100° C. oven for 10 minutes. The flexibility of the dermal patch was tested with the above described procedure.

(B) Seven and one-half parts of AIRVOL 350 were mixed with 92.3 parts of distilled water and 0.2 parts of preservative. The mixture was heated to 94° C. and agitated at this temperature for 1 hour. The poly(vinyl) alcohol solution was cooled to room temperature. A dermal patch was formed following Example 10 (A). The flexibility of the dermal patch was tested with the above described procedure and the results are shown in Table 3 below.

TABLE 3

RESULTS OF DRAPE TEST OF EXAMPLE 10

| Average Molecular Weight | Polymer Concentration Weight # | Catalyst Concentration Weight % of Titanium | Drape Distance (d) mm |
|---|---|---|---|
| 115,500 | 7.5 | 0.15 | 5.5 |
| 155,000 | 7.5 | 0.15 | 9.5 |

EXAMPLE 11

Pharmaceutically Active Agent

In this example, the incorporation of a pharmaceutically active agent such as silver sulfadiazine was demonstrated. This antibacterial agent is especially well suited for the topical therapy of burn wounds.

A dispersion was prepared by adding 2.5 parts of AIRVOL 350 and 5 parts of AIRVOL 425 in 91.25 parts of distilled water. To this mixture were added 0.15 parts of potassium sorbate and 1.0 part of potassium hydrogen phthalate. The mixture was heated to 93° C. and stirred for one hour at this temperature. The resulting solution was cooled to 50° C. and 0.1 part of GERMALL II was added. The solution was cooled to room temperature. The pH of the resulting solution was 4.7. In 100 parts of this solution 1 part of silver sulfadiazine was added and adequately mixed to form a homogeneous dispersion. Ten parts of the above solution were mixed with 1 part of cross linking solution A. A 125 mil thick dermal patch was drawn onto a thin polyurethane substrate. The film was placed in a 100° C. oven for 7 minutes. The film was white, the silver sulfadiazine was uniformly distributed in the hydrogel. The film was dry to the touch and had good strength. Small disks (2.2 mm diameter) were cut from the dermal patch and placed into a vial with 20 ml of balanced salt solution. The vial was placed for one hour on a shaker. After the hour long extraction the solution was tested for its silver content. It was determined that 1% by weight of the silver contained in the dermal patch was released within the first hour of extraction.

Although the invention has been described above with respect to specific aspects, it is intended that other aspects which are not specifically described herein, such as for example, the use of multivalent elements other than those specifically described herein, the use of copolymers not specifically described herein, the use of pharmaceutically active agents not specifically described herein, the use of other additives not specifically described herein, and the like, be included within the scope of the claims which follow.

We claim:

1. A dermal patch comprising:

a) an outer surface;

b) an inner surface which is removably adherent to a dermal surface of a mammal;

c) an internal matrix disposed between the inner surface and the outer surface, said internal matrix comprising a flexible, crosslinked polymeric gel comprising;
  (i) from about 2 to 14 weight percent of polyvinyl alcohol, said polyvinyl alcohol having
    (1) a molecular weight of from about 31,000 to 186,000 g/gmole; and
    (2) a degree of hydrolysis of at least about 88%; and
  (ii) from about 1.6 to 11 weight percent of a crosslinking agent comprising a titanium complex selected from the group consisting of;
    (i) titanium complexes with tri(hydroxyalkyl)amines containing from 2 to 6 carbon atoms; and
    (ii) titanium complexes with diketones containing from 5 to 20 carbon atoms; and
    (iii) from about 25 to 95 weight percent water.

2. The patch of claim 1 wherein the polyvinyl alcohol has a molecular weight of from about 90,000 to 130,000 g/gmole.

3. The patch of claim 1 wherein the polyvinyl alcohol has a degree of hydrolysis of from about 96 to 99%.

4. The patch of claim 1 wherein the polymeric gel comprises from about 1.6 to 3.2 weight percent of the crosslinking agent.

5. The patch of claim 1 wherein the internal matrix further comprises a pharmaceutically active ingredient.

6. The patch of claim 1 wherein the dermal patch has a Draping Distance of less than 7 millimeters.

7. The patch of claim 1 wherein the multivalent transition element is effective to promote the crosslinking of the polyvinyl alcohol at a pH of from about 4 to 8.

8. The patch of claim 1 wherein the multivalent transition element is effective to promote the crosslinking of the polyvinyl alcohol at a pH of from about 5.0 to 7.0.

9. A dermal patch comprising:
a) an outer surface;
b) an inner surface which is reasonably adherent to a dermal surface of a mammal;
c) an internal matrix disposed between the inner surface and the outer surface, said internal matrix comprising a flexible, crosslinked polymeric gel comprising;
  (i) from about 5 to 9 weight percent of polyvinyl alcohol, said polyvinyl alcohol having
    (1) a molecular weight of from about 85,000 to 186,000 g/gmole; and
    (2) a degree of hydrolysis of from about 96 to 99%; and
  (ii) from about 1.6 to 3.2 weight percent of a crosslinking agent comprising a titanium complex selected from the group consisting of;
    (1) titanium complexes with tri(hydroxyalkyl) amines containing from 2 to 6 carbon atoms, and
    (2) titanium complexes with diketones containing from 5 to 20 carbon atoms; and
  (iii) from about 75 to 95 weight percent water.

* * * * *